(12) United States Patent
Moore

(10) Patent No.: US 10,932,965 B2
(45) Date of Patent: Mar. 2, 2021

(54) SYSTEMS AND METHODS FOR CONFIGURING A WHEELCHAIR

(71) Applicant: Toyota Motor Engineering & Manufacturing North America, Inc., Erlanger, KY (US)

(72) Inventor: Douglas A. Moore, Fairview, TX (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 476 days.

(21) Appl. No.: 15/885,181

(22) Filed: Jan. 31, 2018

(65) Prior Publication Data

US 2019/0231619 A1 Aug. 1, 2019

(51) Int. Cl.
| | |
|---|---|
| *A61G 5/10* | (2006.01) |
| *B60L 15/20* | (2006.01) |
| *A61G 5/04* | (2013.01) |
| *A61B 5/00* | (2006.01) |
| *G16H 40/67* | (2018.01) |
| *G16H 70/20* | (2018.01) |

(52) U.S. Cl.
CPC .............. *A61G 5/10* (2013.01); *A61B 5/6894* (2013.01); *A61G 5/04* (2013.01); *A61G 5/045* (2013.01); *B60L 15/20* (2013.01); *G16H 40/67* (2018.01); *G16H 70/20* (2018.01); *A61G 5/047* (2013.01); *A61G 2203/10* (2013.01); *A61G 2203/12* (2013.01); *A61G 2203/16* (2013.01); *B60L 2200/34* (2013.01)

(58) Field of Classification Search
CPC . A61G 5/10; A61G 5/04; A61G 5/045; A61B 5/6894; G16H 40/67; G16H 70/20; B60L 15/20

USPC .......................................................... 180/6.2
See application file for complete search history.

(56) References Cited

U.S. PATENT DOCUMENTS

| | | | | |
|---|---|---|---|---|
| 6,050,356 | A  * | 4/2000 | Takeda | A61G 5/045 |
| | | | | 180/65.1 |
| 10,130,533 | B2 * | 11/2018 | Schneider | A61G 5/10 |
| 10,543,741 | B2 * | 1/2020 | Biderman | B60L 58/21 |
| 10,627,826 | B2 * | 4/2020 | Moore | A61G 5/04 |
| 2005/0279539 | A1 * | 12/2005 | Chiou | B60K 1/00 |
| | | | | 180/65.1 |

(Continued)

OTHER PUBLICATIONS

Carrington et al.; "Wearables and chairables: inclusive design of mobile input and output techniques for power wheelchair users"; ACM Digital Library; URL: https://dl.acm.org/citation.cfm?id=2611247.2557237; 2014.

(Continued)

*Primary Examiner* — Jacob D Knutson
(74) *Attorney, Agent, or Firm* — Dinsmore & Shohl LLP

(57) ABSTRACT

Systems and methods for configuring a wheelchair are provided. One embodiment of a method includes receiving a passenger-specific setting for the wheelchair, determining that a chair component of the wheelchair is removably coupled to a power base component, and in response to determining that the chair component and the power base component are coupled, communicating the passenger-specific setting to the chair component. In some embodiments, in response to receiving the passenger-specific setting, implementing the passenger-specific setting, where implementing the passenger-specific setting includes altering a physical property of the wheelchair.

20 Claims, 5 Drawing Sheets

(56) References Cited

U.S. PATENT DOCUMENTS

| | | | |
|---|---|---|---|
| 2007/0051543 A1* | 3/2007 | Kamen | A61G 5/1059 |
| | | | 180/65.1 |
| 2016/0213535 A1* | 7/2016 | Maither | A61G 5/14 |
| 2016/0363449 A1 | 12/2016 | Metzler et al. | |
| 2017/0071812 A1 | 3/2017 | Sandler et al. | |
| 2017/0240169 A1* | 8/2017 | Coulter | B60L 50/60 |
| 2017/0259811 A1 | 9/2017 | Coulter et al. | |
| 2017/0300058 A1 | 10/2017 | Peret et al. | |

OTHER PUBLICATIONS

Harris, Miriam; "Best smartwatches, bands and trackers for wheelchair fitness tracking"; Macworld UK; URL: https://www.macworld.co.uk/feature/apple/alternativesapple-watch-for-wheelchairfitness-tracking-3642622/; 2016.

* cited by examiner

SYSTEMS AND METHODS FOR CONFIGURING A WHEELCHAIR

TECHNICAL FIELD

Embodiments described herein generally relate to systems and methods for configuring a wheelchair. And, more specifically, to embodiments that utilize a smart device and/or wearable device for configuring a powered wheelchair.

BACKGROUND

There are a variety of powered wheelchairs in the market and while they each vary in capabilities, most powered wheelchairs can be customized to the specific user in both fit and function. As an example, some powered wheelchairs are modular and include a chair component and a power base component. While this modular approach to wheelchair design can be beneficial, currently nothing in the market provides for customizable functionality and interchangeability of wheelchair components. As such, a need exists in the industry.

SUMMARY

Systems and methods for configuring a wheelchair are provided. One embodiment of a method includes receiving a passenger-specific setting for the wheelchair, determining that a chair component of the wheelchair is removably coupled to a power base component, and in response to determining that the chair component and the power base component are coupled, communicating the passenger-specific setting to the chair component. In some embodiments, in response to receiving the passenger-specific setting, implementing the passenger-specific setting, where implementing the passenger-specific setting includes altering a physical property of the wheelchair.

In another embodiment, a modular powered wheelchair system includes a chair component with a base-receiving interface, where the chair component receives a passenger and a passenger-specific setting. The system may also include a power base component with a chair-receiving interface that removably receives the base-receiving interface of the chair component, where the power base component further includes a plurality of wheels for causing the wheelchair to traverse an environment. The system may also include a computing device that stores logic that causes the modular powered wheelchair system to determine that the chair component and the power base component are coupled. In response to determining that the chair component and the power base component are coupled, the logic may cause the system to communicate the passenger-specific setting to the chair component, where in response to receiving the passenger-specific setting, the chair component implements the passenger-specific setting.

In yet another embodiment, modular powered wheelchair system includes a chair component with a base-receiving interface, where the chair component receives a passenger and a passenger-specific setting. The system may also include a computing device that is coupled to the chair component and stores logic that causes the modular powered wheelchair system to determine that the chair component and the power base component are coupled. In some embodiments, in response to determining that the chair component and the power base component are coupled, the logic may cause the system to communicate the passenger-specific setting to the chair component, where in response to receiving the passenger-specific setting, the chair component implements the passenger-specific setting.

These and additional features provided by the embodiments of the present disclosure will be more fully understood in view of the following detailed description, in conjunction with the drawings.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which.

DETAILED DESCRIPTION

Embodiments disclosed herein include systems and methods for configuring a wheelchair. Many powered wheelchairs can be used in a variety of environments and perform a variety of different movements, depending on the terrain and the user. This typically requires the wheelchair to have various settings or calibrations to coordinate appropriate mobility. For example, balancing, geo-fencing, speed limitations, height, weight distribution, age, skill level, and the like may all be customized to the user. Certain calibrations may also be required based on the physiological state of the passenger, the health of the passenger, and/or prescriptions of the passenger. Prescriptions may be defined by a third party, such as a physician or physical therapist.

Some embodiments include a portable device, such as a smart phone, tablet, or smart wearable (watch, bracelet, ring, etc.) that may be paired with a controller, processor, or equivalent control unit of the power base component. In one aspect, the portable device can include an application that syncs with the power base component via a wired or wireless connection. Settings can be saved in the application and transferred to the power base component (and/or on the power base component). The application may reside locally on the portable device and communicate via a network or cloud to obtain different calibration settings for a particular user.

In some embodiments, settings can be transferred through a network or cloud based system, directly to the power base. In various aspects, a physician (or person having appropriate credentials) can update or prescribe calibrations to the powered wheel chair remotely. The systems and methods for configuring a wheelchair incorporating the same will be described in more detail, below.

Figure 1:
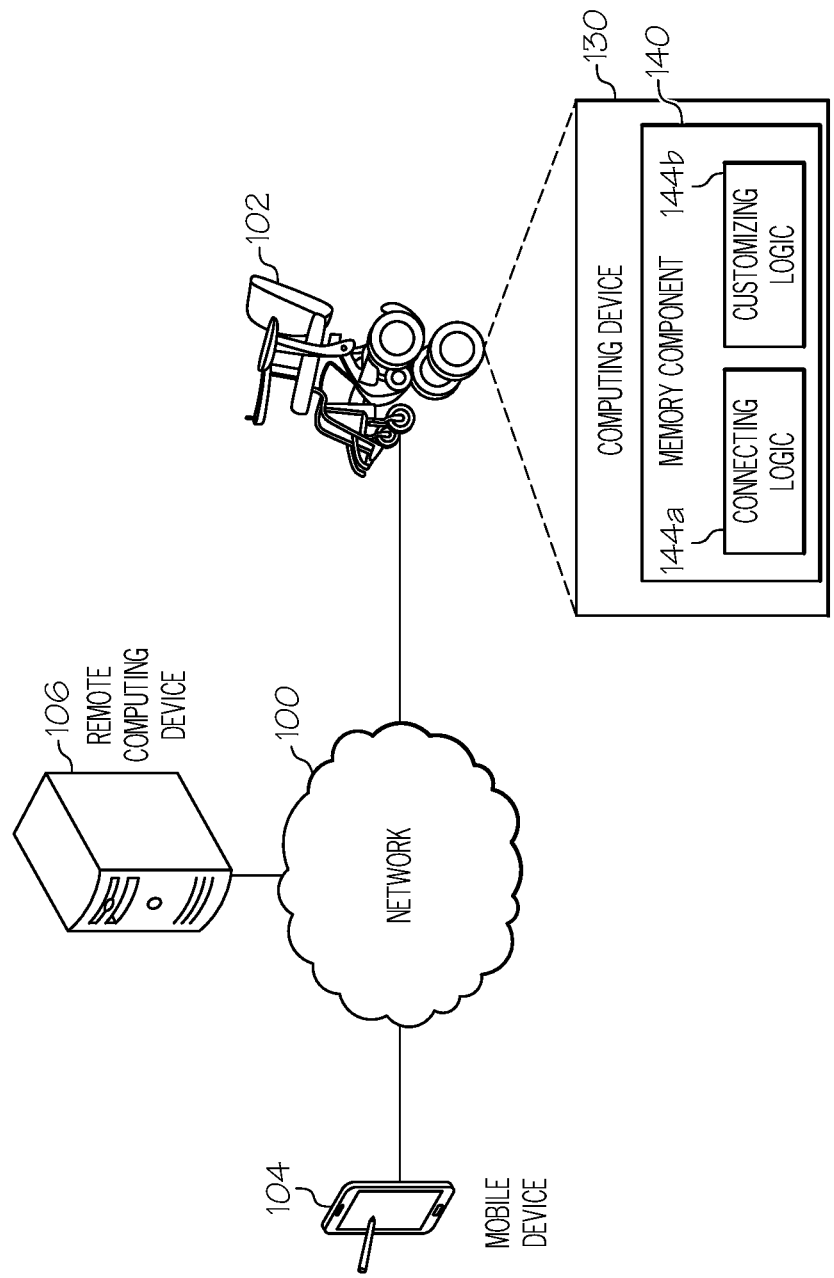
FIG. 1 depicts a computing environment for configuring a wheelchair, according to embodiments described herein.

Referring now to the drawings, FIG. 1 depicts a computing environment for configuring a wheelchair, according to embodiments described herein. As illustrated, the computing environment includes a network 100. The network 100 may include a wide area network (WAN), such as the internet, a public switched telephone network, a cellular network, a mobile data network, and/or the like, such as via (WiMax, LTE, 4G, 5G,etc.). The network 100 may include a local wired network (such as via Ethernet, etc.), a local wireless network (such as via Wi-Fi, etc.). The network 100 may similarly facilitate direct device-to-device communication, such as via Bluetooth, Zigbee, etc. Regardless, the network 100 may be configured to couple a wheelchair 102, a mobile device 104, and a remote computing device 106.

The wheelchair 102 may be any powered device for receiving a passenger and accommodating for at least one physical attribute. The wheelchair 102 may include a wheelchair computing device, such as computing device 130, which may include a memory component 140. The memory component 140 may store connecting logic 144a and customizing logic 144b. The connecting logic may facilitate connecting of a chair portion of the wheelchair 102 with a power base portion, as described in more detail below. The customizing logic 144b may be configured to implement a passenger-specific setting of the wheelchair 102. As discussed in more detail below, implementing the passenger-specific setting may include determining a current state of the physical property of the wheelchair 102 to determine whether to implement the passenger-specific setting and/or altering any physical property of the wheelchair 102. As an example, the passenger-specific settings may be associated with balancing, geo-fencing, speed limitations, height, weight distribution, age, skill level, and/or prescriptions of the passenger. As will be understood, the passenger-specific settings may be stored on the computing device 130, the mobile device 104 and/or the remote computing device 106.

The mobile device 104 may be configured as a mobile phone, tablet, laptop, personal computer, and/or other device for providing the functionality described herein. The mobile device 104 may be configured for storing passenger-specific settings of the wheelchair 102 and communicating the passenger-specific settings to the computing device 130. Additionally, the mobile device 104 may be configured for receiving the passenger-specific settings from a user and/or healthcare provider. As such, the mobile device 104 may represent a device carried by the wheelchair passenger and/or a computing device accessed by a healthcare provider.

The remote computing device 106 may be configured to communicate with the mobile device 104 and/or the computing device 130. The remote computing device 106 may be configured as a personal computer, server, laptop, mobile computing device, and/or other device for communicating and/or storing data associated with the passenger-specific settings. As such, the remote computing device 106 may be utilized merely to store and communicate data (such as prescriptions, location data, etc.) with the computing device 130 and/or may be configured for communicating settings to the mobile device 104.

Figure 2:
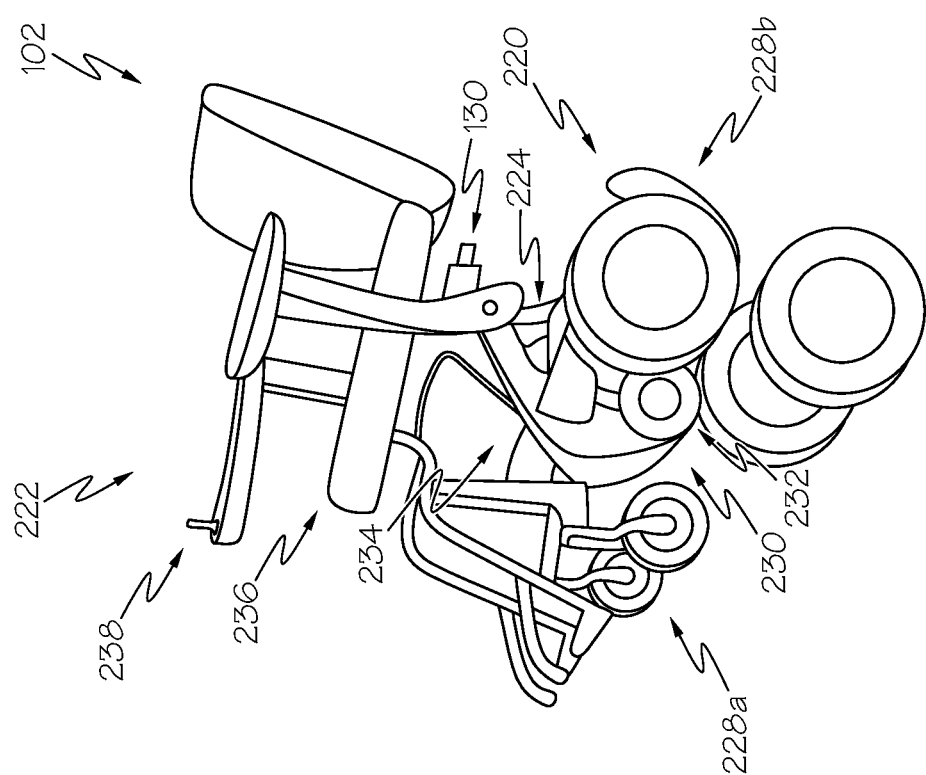
FIG. 2 depicts a perspective view of a wheelchair, according to embodiments described herein.

FIG. 2 depicts a perspective view of a wheelchair 102, according to embodiments described herein. As illustrated, the wheelchair 102 includes a power base component 220 and a chair component 222. The power base component 220 may include a chair-receiving interface 224, a plurality unpowered wheels 228a, a plurality of powered wheels 228b, a battery 230, a motor 232, and the computing device 130. The chair-receiving interface 224 may be configured as a male, female, or other type of physical connector for receiving a base-receiving interface 234 of the chair component 222. The base-receiving interface 234 may be oppositely configured from the chair-receiving interface 224 such that a physical connection between the chair-receiving interface 224 and the base-receiving interface 234 removably secures the power base component 220 to the chair component 222. Additionally, the chair-receiving interface 224 may also facilitate communication and/or an electrical connection between the power base component 220 and the chair component 222 to facilitate powering of the chair component 222 and/or communicating data between the power base component 220 and the chair component 222.

It should be understood that while the computing device 130 is depicted as being part of the power base component 220, this is merely an example. Depending on the embodiment, data and settings described herein may be stored on the power base component 220, the chair component 222, on the mobile device 104, on the remote computing device 106, and/or elsewhere.

Additionally, the chair component 222 may include the base-receiving interface 234, as well as a seat portion 236, and a controller portion 238. In some embodiments, the chair component 222 may also be powered. The seat portion 236 may include one or more sensors, including weight sensors, proximity sensors, heat sensors, gyroscopes, etc. for determining the position of a passenger. Biometric sensors may also be included, such as heart rate monitors, temperature sensors, blood pressure sensors, imaging devices, computer-brain interface, etc. for determining a physiological state of the passenger. The controller portion 238 may include a joystick, a mouth control, and/or other mechanism for controlling the wheelchair 102.

It should be understood that while the chair component 222 (including the seat portion 236) may be configured as a traditional chair, this is merely one example. In some embodiments, the chair component 222 and/or the seat portion 236 may be configured as an exoskeleton, standing component, brain interface device, and/or other configuration for enhancing the physical capabilities of the passenger.

Movement of a wheelchair 102 may be facilitated via the controller portion 238 and implemented by sophisticated sensors and gyroscopes to maintain the unit's balance while climbing up and down stairs, curbs, and varied terrain. Among other things, the wheelchair 102 can raise a seated passenger to eye-level standing height, and balance and travel on two wheels.

Figure 3:
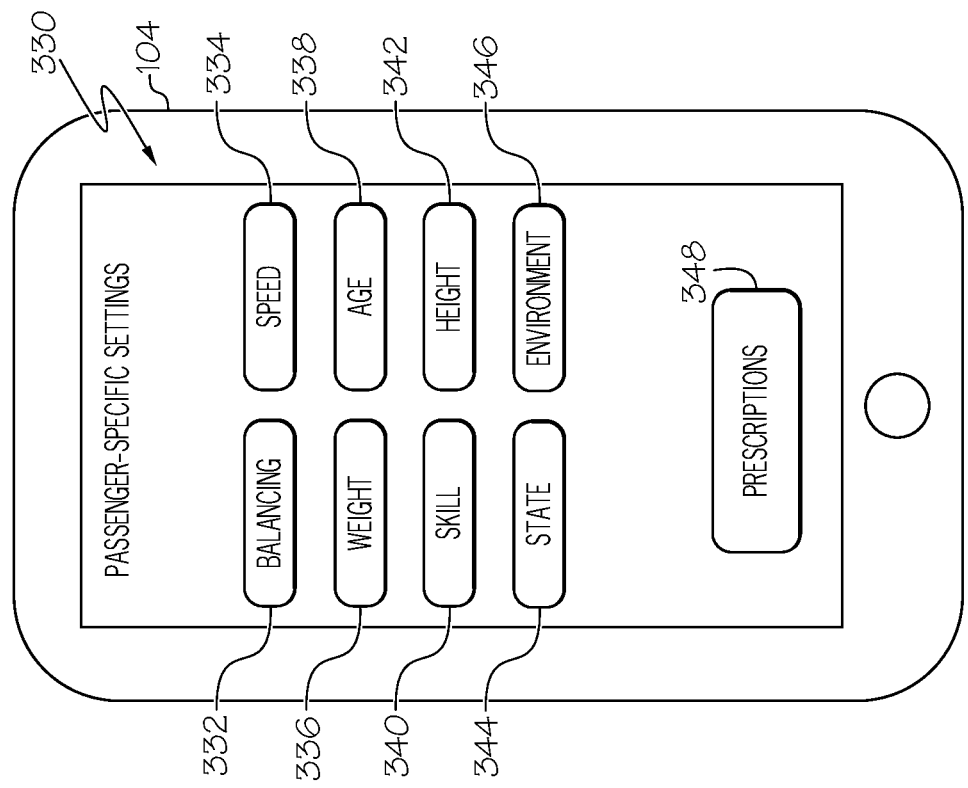
FIG. 3 depicts a user interface of passenger-specific settings of a wheelchair, according to embodiments described herein.

FIG. 3 depicts a user interface 330 of passenger-specific settings of a wheelchair 102, according to embodiments described herein. As discussed above, embodiments described herein may be configured to automatically customize a chair component 222 and/or a power base component 220, based on predetermined settings and/or prescriptions for a passenger. Specifically, embodiments described herein may be configured such that a new chair component may be received by a power base component 220 and the power base component 220 communicate passenger-specific settings to be implemented by the chair component 222 As such, the user interface 30 may provide options for assigning values to the passenger-specific settings. As an example, the user interface 330 may include a balancing option 332, a speed option 334, a weight option 336, an age option 338, a skill option 340, a height option 342, a state option 344, and an environment option 346. Also provided in the user interface 330 is a prescriptions option 348.

In response to selection of the balancing option 332, the mobile device 104 may provide one or more options for the user to define balancing features of the wheelchair 102. As an example, based on the passenger's posture, the balance of the wheelchair 102 may change to maintain the chair portion 222 is consistent in its orientation, relative to ground. The balancing features may be manually entered by the user (such as height, weight, etc.) and/or may be determined via sensors on the wheelchair 102. As an example, the sensors on the wheelchair 102 may determine the height, weight, weight distribution, eye position, etc. of the user (stationary and in motion) to calibrate the balancing features of the wheelchair 102. Once the balancing features are set, options for the user to adjust the balancing features and/or passenger parameters to more accurately represent the desired operation of the wheelchair 102.

In response to selection of the speed option 334, speed characteristics may be set. Speed characteristics may include a maximum speed, an acceleration response, a maximum acceleration rate, and/or other settings related to the speed of the wheelchair 102. As an example, if the passenger is new to the wheelchair 102 or if the physical or mental condition of the passenger necessitates, the maximum speed of the wheelchair 102 may be limited to a predetermined rate (generally and/or in predetermined locations). The other speed characteristics may also be adjusted accordingly.

In response to selection of the weight option 336, the weight of the passenger may be input. By setting the weight, other performance-based characteristics of the wheelchair 102 may also be adjusted. It should also be understood that while the weight of the passenger may be manually set, some embodiments may be configured to determine the weight of the passenger via a weight sensor on the wheelchair 102 itself. Similarly, while the weight setting 336 may be configured for the user to identify the passenger's weight, some embodiments may be configured for the user to identify the total weight of any other payload on the wheelchair 102, as well.

In response to selection of the age option 338, the user may indicate the passenger's age. The passenger's age may be further utilized to affect one or more performance characteristics of the wheelchair 102. As an example, some embodiments may be configured to geofence the passenger, based on age, physical limitations, and/or other settings to prevent the passenger from going to one or more predetermined areas.

In response to selection of the skill option 340, the user may indicate the passenger's skill with the wheelchair 102. The skill level may be based on a length of time with the wheelchair 102, based on a test taken by the passenger, and/or based on other criteria. As with some of the other settings discussed herein, the skill level may automatically populate one or more other settings described herein. As an example, one or more speed characteristics may be automatically populated based the determined skill of the passenger. Similarly, some embodiments may provide options for a user to select a skill level of the passenger.

In response to selection of the height option 342, the user may enter the passenger's height. This may be utilized when the wheelchair 102 height is adjusted, such that the passenger is at a desired height (such as at a dinner table, desk, etc.). As described above, some embodiments may be configured to automatically determine the passenger's height and make adjustments accordingly.

In response to selection of the prescriptions option 348, the user may create, view, and/or edit prescriptions for the passenger in his/her use of the wheelchair 102. While the user may have permissions to view and validate completion of the prescriptions, the prescriptions themselves may be restricted from creation and editing except by a healthcare provider. This is described in more detail with reference to FIG. 4.

In response to selection of the state option 344, further options for a user to define passenger physiological states that may be utilized by the wheelchair 102. As an example, some embodiments may monitor the physiological state of the passenger, such as heart rate, blood pressure, eye dilation, voice patterns, etc. Based on settings implemented in response to selection of the state option 344, the user may alter operation and/or functionality of the wheelchair 102, based on a threshold condition of the particular physiological state. As an example, if the heart rate of the passenger exceeds a predetermined threshold, control of the wheelchair 102 may be altered (e.g., maximum speed may be reduced). Similarly, the biometric sensors may be utilized to determine that the passenger is experiencing a medical condition (e.g., stroke, heart attack, etc.) and report the condition to an appropriate health provider (in addition to restricting functionality). The determined biometric condition may also be used for geo-fencing, as described with regard to the environment option 346.

In response to selection of the environment option 346, options may be provided for altering operation of the wheelchair 102, based on a location of the wheelchair 102. As an example, this geo-fencing functionality may be static in that the passenger and/or wheelchair 102 may be restricted from a static location or type of location (e.g., restrictions from crossing a particular street or any street). The geo-fencing functionality may also be configured to restrict where the wheelchair 102 may go, based on time of day, physiological state of the passenger, and/or other criteria.

It should also be understood that the term "passenger" is utilized herein to indicate a person that uses the wheelchair 102. The term "user" is utilized herein to indicate a user of the mobile device 104. As will be recognized, in some embodiments the user and passenger are separate people/entities. However, some embodiments may be configured such that the passenger of the wheelchair 102 is also the user of the mobile device 104.

Figure 4:
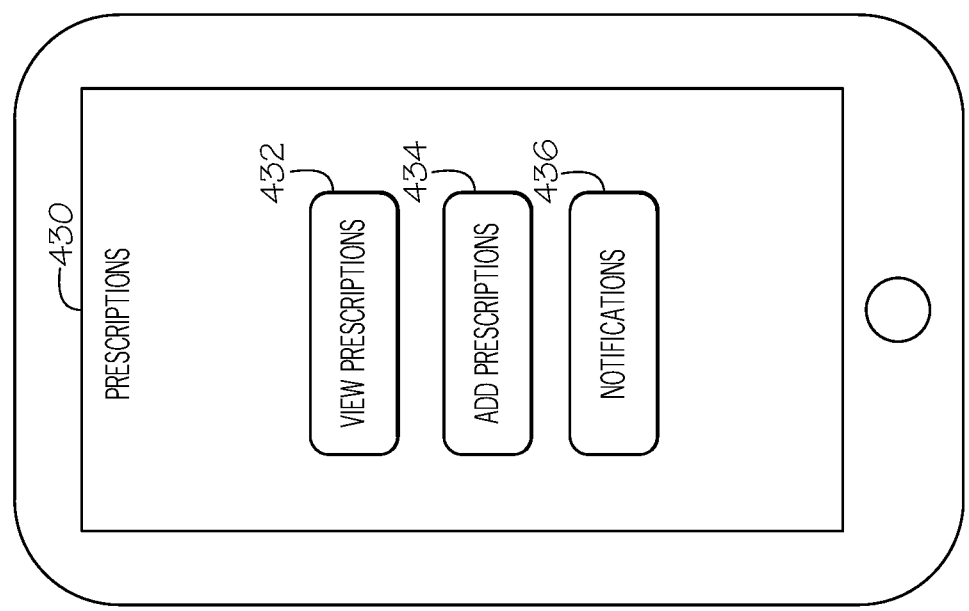
FIG. 4 depicts a user interface for providing options related to prescriptions for a wheelchair, according to embodiments described herein.

FIG. 4 depicts a user interface 430 for providing options related to prescriptions for a wheelchair 102, according to embodiments described herein. In response to selection of the prescriptions option 348, the user interface 430 may be provided. Included in the user interface 430 are a view prescriptions option 432, an add prescriptions option 434, and a notifications option 436. In response to selection of the view prescriptions option 432, one or more prescriptions for the passenger may be provided. As described in more detail below, the prescriptions may relate to restrictions on use of the wheelchair 102, physical therapy prescriptions, and/or other activities related to the wheelchair 102.

In response to selection of the add prescriptions option 434, prescriptions may be added, removed, and/or edited. In some embodiments, only a healthcare provider may add a prescription. However some embodiments may be configured such that the healthcare provider remotely enters a prescription for the user to activate or associate with the passenger via the add prescriptions option 434.

In response to selection of the notifications option 436, the user may view, create, edit, and/or remove notification settings associated with the passenger's prescriptions. As an example, some embodiments may be configured to send a push notification to the mobile device when the passenger receives a new prescription. As another example, a notification may be sent when the passenger completes a physical therapy and/or a prescription otherwise expires. Other notifications may also be provided.

Figure 5:
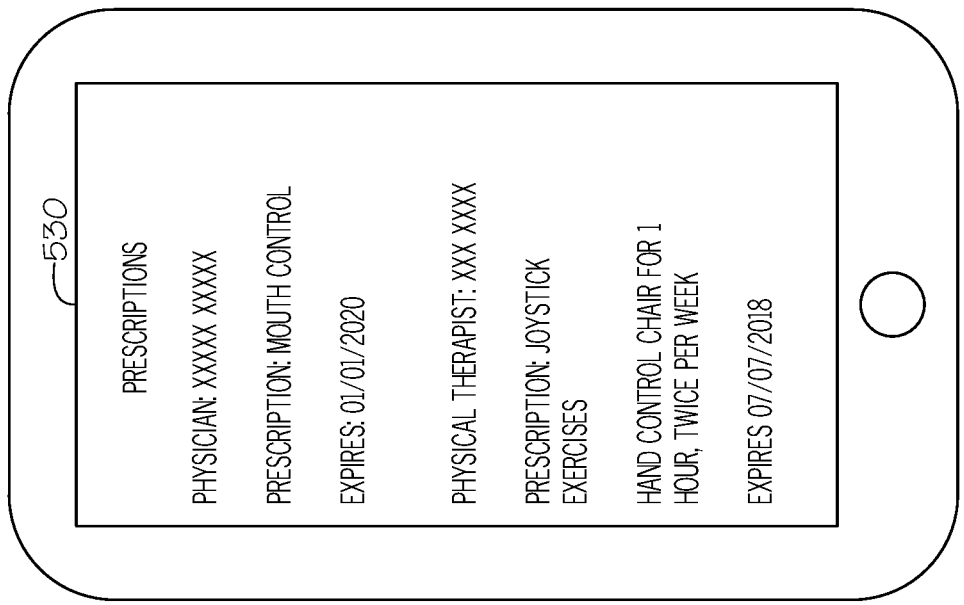
FIG. 5 depicts a user interface for providing prescription details, according to embodiments described herein.

FIG. 5 depicts a user interface 530 for providing prescription details, according to embodiments described herein. As illustrated, the user interface 530 provides details of prescriptions that have been issued to the passenger of the wheelchair 102. As described above, the prescription may be written by a physician, a physical therapist, and/or other healthcare provider that is authorized to issue such a prescription. As such, the prescriptions depicted in FIG. 5 include a prescription to use the mouth controller of the wheelchair 102 until Jan. 1, 2020. As such, the wheelchair 102 may be configured to disable a joystick controller and only allow control via the mouth controller. After Jan. 1, 2020, the restriction on the operation of the wheelchair 102 may be removed.

Also provided in the user interface 530 is a physical therapy prescription. The physical therapy prescription may include exercises that the passenger should perform. As an example, the user interface 530 provides that the passenger should use the hand controller for one hour, twice per week. In some embodiments, the passenger and/or use may schedule this time, while some embodiments may be configured for automatic scheduling. As an example, the wheelchair 102 may determine (such as from an electronic calendar of the passenger) a time for the passenger to perform the exercises. The wheelchair 102 may then disable functionality such that the passenger can only operate the wheelchair 102 according to the prescribed exercises. The wheelchair 102 may also be configured to account for the exercises that the passenger actually performs to determine whether the passenger has completed the prescription. This can be reported back to the healthcare professional.

Figure 6:
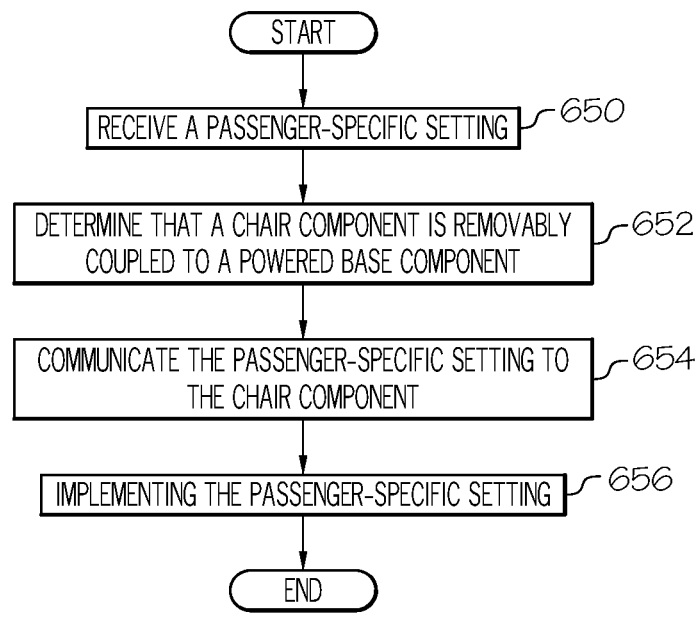
FIG. 6 depicts a flowchart for configuring a wheelchair, according to embodiments described herein.

FIG. 6 depicts a flowchart for configuring a wheelchair 102, according to embodiments described herein. As illustrated in block 650, a passenger-specific setting for the wheelchair 102 may be received. In block 652, a determination may be made that the chair component 222 of the wheelchair 102 is removably coupled to a power base component 220. In block 654, in response to determining that the chair component 222 and the power base component 220 are coupled, the passenger-specific setting may be communicated to the chair component 222. In block 656, in response to receiving the passenger-specific setting, the passenger-specific setting may be implemented via the chair component 222, where implementing the passenger-specific setting includes altering a physical property of the wheelchair 102.

Figure 7:
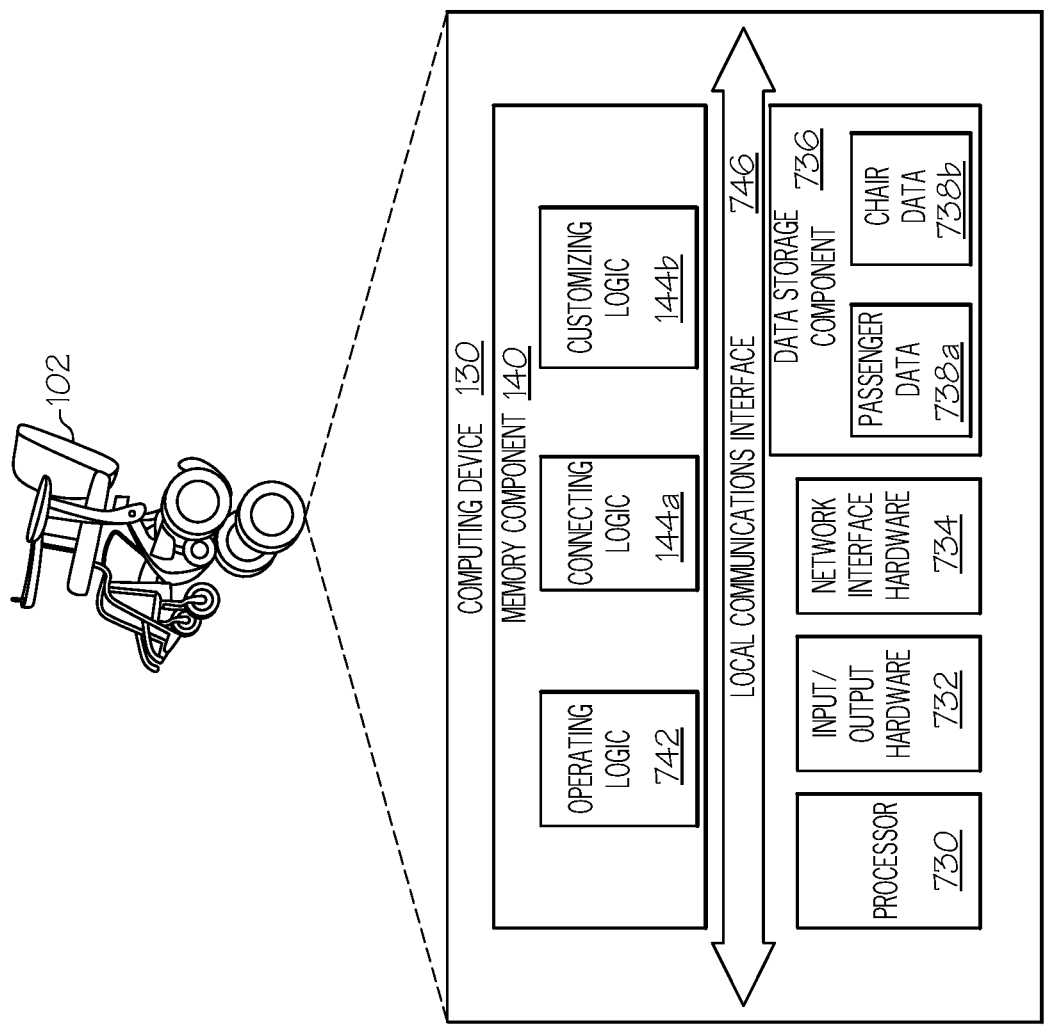
FIG. 7 depicts details of a computing device of a wheelchair, according to embodiments described herein.

FIG. 7 depicts details of a computing device 130 of a wheelchair 102, according to embodiments described herein. The computing device 130 includes a processor 730, input/output hardware 732, the network interface hardware 734, a data storage component 736 (which stores passenger data 738a, chair data 738b, and/or other data), and the memory component 140. The memory component 140 may be configured as volatile and/or nonvolatile memory and as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the computing device 130 and/or external to the computing device 130.

The memory component 140 may store operating logic 742, the connecting logic 144a and the customizing logic 144b. The connecting logic 144a and the customizing logic 144b may each include a plurality of different pieces of logic, each of which may be embodied as a computer program, firmware, and/or hardware, as an example. A local communications interface 746 is also included in FIG. 7 and may be implemented as a bus or other communication interface to facilitate communication among the components of the computing device 130.

The processor 730 may include any processing component operable to receive and execute instructions (such as from a data storage component 736 and/or the memory component 140). As described above, the input/output hardware 732 may include and/or be configured to interface with the components of the wheelchair 102.

The network interface hardware 734 may include and/or be configured for communicating with any wired or wireless networking hardware, including an antenna, a modem, LAN port, wireless fidelity (Wi-Fi) card, WiMax card, Bluetooth chip, USB card, mobile communications hardware, and/or other hardware for communicating with other networks and/or devices. From this connection, communication may be facilitated between the computing device 130 and other computing devices, such as via the internet, to provide the functionality described herein.

The operating logic 742 may include an operating system and/or other software for managing components of the computing device 130. As also discussed above, the content connecting logic 144a may reside in the memory component 140 and may be configured to cause the processor 730 provide facilitate communication between the chair component 222 and the power base component 220. In some embodiments, the connecting logic 144a may facilitate communication between the wheelchair 102 and eternal components, such as the mobile device 104 and/or the remote computing device 106. Similarly, the customizing logic 144b may be utilized to customize the chair component 222, as described above.

It should be understood that while the components in FIG. 7 are illustrated as residing within the computing device 130, this is merely an example. In some embodiments, one or more of the components may reside external to the computing device 130. It should also be understood that, while the computing device 130 is illustrated as a single device, this is also merely an example. In some embodiments, the connecting logic 144a and the customizing logic 144b may reside on different computing devices. As an example, one or more of the functionality and/or components described herein may be provided by another computing device, such as the mobile device 104, the remote computing device 106, etc.

Additionally, while the computing device 130 is illustrated with the connecting logic 144a and the customizing logic 144b as separate logical components, this is also an example. In some embodiments, a single piece of logic may cause the computing device 130 to provide the described functionality.

As illustrated above, various embodiments for configuring a wheelchair are disclosed. These embodiments may be configured such that a user/passenger is able to exchange different chair components with a powered-base component, as well as transfer data and settings to fully customize the new configurations.

While particular embodiments and aspects of the present disclosure have been illustrated and described herein, various other changes and modifications can be made without departing from the spirit and scope of the disclosure. Moreover, although various aspects have been described herein, such aspects need not be utilized in combination. Accordingly, it is therefore intended that the appended claims cover all such changes and modifications that are within the scope of the embodiments shown and described herein.

It should now be understood that embodiments disclosed herein include systems, methods, and non-transitory computer-readable mediums for configuring a wheelchair. It should also be understood that these embodiments are merely exemplary and are not intended to limit the scope of this disclosure.

What is claimed is:

1. A method for configuring a wheelchair, comprising:
receiving, by a computing device, a passenger-specific setting for a passenger of the wheelchair;
determining, by the computing device, that a chair component of the wheelchair is removably coupled to a power base component;
in response to determining that the chair component and the power base component are coupled, communicating, by the computing device, the passenger-specific setting to the chair component;
in response to receiving the passenger-specific setting, implementing, via the chair component, the passenger-specific setting, wherein implementing the passenger-specific setting includes altering a physical property of the wheelchair.

2. The method of claim 1, further comprising determining a current state of the physical property of the wheelchair to determine whether to implement the passenger- specific setting.

3. The method of claim 1, wherein the passenger-specific setting includes at least one of the following: balancing, geo-fencing, speed limitations, height, weight distribution, age, skill level, or prescriptions.

4. The method of claim 1, further comprising receiving a prescription from a healthcare provider and implement the prescription on the chair component.

5. The method of claim 1, wherein a physiological state of the passenger is utilized to determine whether to alter operation of the wheelchair.

6. The method of claim 1, wherein the passenger-specific setting is received from a mobile device of the passenger.

7. The method of claim 1, further comprising determining the passenger- specific setting.

8. A modular powered wheelchair system comprising:
a chair component that includes a base-receiving interface, wherein the chair component receives a passenger and a passenger-specific setting;
a power base component that includes a chair-receiving interface that removably receives the base-receiving interface of the chair component, wherein the power base component further includes a plurality of wheels for causing the modular powered wheelchair system to traverse an environment; and
a computing device that stores logic that causes the modular powered wheelchair system to perform at least the following:
determine that the chair component and the power base component are coupled; and
in response to determining that the chair component and the power base component are coupled, communicate the passenger-specific setting to the chair component, wherein in response to receiving the passenger-specific setting, the chair component implements the passenger-specific setting.

9. The modular powered wheelchair system of claim 8, wherein the passenger-specific setting includes at least one of the following: balancing, geo-fencing, speed limitations, height, weight distribution, age, skill level, or prescriptions.

10. The modular powered wheelchair system of claim 8, wherein the logic further causes the modular powered wheelchair system to receive a prescription from a healthcare provider and implement the prescription on the chair component.

11. The modular powered wheelchair system of claim 8, wherein the logic further causes the modular powered wheelchair system to authenticate the power base component.

12. The modular powered wheelchair system of claim 8, wherein the passenger-specific setting is received from a mobile device of the passenger.

13. The modular powered wheelchair system of claim 8, wherein the logic further causes the modular powered wheelchair system to communicate authenticating information to the power base component prior to receiving the power base component.

14. The modular powered wheelchair system of claim 8, further comprising a sensor coupled to the chair component to determine the passenger-specific setting.

15. A modular powered wheelchair system comprising:
a chair component that includes a base-receiving interface, wherein the chair component receives a passenger and a passenger-specific setting; and
a computing device that is coupled to the chair component and stores logic that causes the modular powered wheelchair system to perform at least the following:
determine that the chair component and a power base component are coupled; and
in response to determining that the chair component and the power base component are coupled, communicate the passenger-specific setting to the chair component, wherein in response to receiving the passenger-specific setting, the chair component implements the passenger-specific setting.

16. The modular powered wheelchair system of claim 15, further comprising:
the power base component that includes a chair-receiving interface that removably receives the base-receiving interface of the chair component, wherein the power base component further includes a plurality of wheels for causing the modular powered wheelchair system to traverse an environment.

17. The modular powered wheelchair system of claim 15, wherein the passenger-specific setting includes at least one of the following: balancing, geo-fencing, speed limitations, height, weight distribution, age, skill level, or prescriptions.

18. The modular powered wheelchair system of claim 15, wherein the logic further causes the modular powered wheelchair system to receive a prescription from a healthcare provider and implement the prescription on the chair component.

19. The modular powered wheelchair system of claim 15, wherein the logic further causes the modular powered wheelchair system to authenticate the power base component.

20. The modular powered wheelchair system of claim 15, wherein the passenger-specific setting is received from a mobile device of the passenger.

* * * * *